United States Patent [19]

Jerábek et al.

[11] Patent Number: 5,011,611

[45] Date of Patent: Apr. 30, 1991

[54] METHOD OF SEPARATION OF FURFURAL FROM DILUTED AQUEOUS SOLUTIONS

[75] Inventors: Karel Jerábek; Karel Setínek; Frantisek Kastánek, all of Praha, Czechoslovakia

[73] Assignee: Ceskoslovenska akademie ved, Praha, Czechoslovakia

[21] Appl. No.: 452,269

[22] Filed: Dec. 15, 1989

[30] Foreign Application Priority Data

Dec. 16, 1988 [CS] Czechoslovakia ............... 8371-88

[51] Int. Cl.$^5$ .............................................. B01D 15/00
[52] U.S. Cl. .................................. 210/674; 210/692; 549/490
[58] Field of Search ................. 210/674, 692; 549/490

[56] References Cited

U.S. PATENT DOCUMENTS 3,531,463  9/1970  Gustafson ......................... 210/674
4,071,398  1/1978  Baierl ............................... 210/674

Primary Examiner—Ivars Cintins
Attorney, Agent, or Firm—Leydig, Voit & Mayer

[57] ABSTRACT

Furfural is separated from a dilute aqueous solution by contacting the solution with a polymer adsorbent which comprises porous crosslinked copolymers of styrene and derivatives thereof, having an internal surface area greater than 30 m$^2$/g and subsequently desorbing furfural from the adsorbent through contact with an alcohol containing from 1 to 3 carbon atoms.

1 Claim, No Drawings

METHOD OF SEPARATION OF FURFURAL FROM DILUTED AQUEOUS SOLUTIONS

The invention concerns the method of separation of furfural from diluted aqueous solutions.

Furfural is manufactured by acid hydrolysis of plant residues. This process produces diluted aqueous solutions in which furfural is contained in concentration as low as 1%. Common methods of furfural separation from these solutions are distillation and extraction by suitable solvents. (Encyklopedia of Chemical Procesing and Design, Marcel Dekker Inc., vol. 24, p. 53, New York 1986) Both methods have serious disadvantages. Distillation of aqueous furfural solutions is complicated by the formation of the azeotrope which at the atmospheric pressure contains approx. 36% of furfural. After condensation the azeotrope separates into two layers, the aqueous one is recirculated and from the remaining one liquid pure furfural is obtained in the second distillation step. Of course, for such process substantial initial investments are required and also the consumption of energy is high. The first distillation step is possible to replace by extraction using a suitable solvent immiscible with water. In this case, the complications are caused by traces of the extracting solvent in waste waters.

For the separation of furfural from aqueous solution some applications of solid adsorbents were also proposed. Known possible adsorption materials are: charcoal (Y. I. Khol'kin, A. I. Karpusheva: Zh. Priklad. Khim. 38, 226 (1965)), wood chips (USSR Pat. No. SU 670,572) and ion exchangers (Hung. Pat. No. T033133). Preparation of mechanically stable packing for efficient adsorption column from charcoal or wood chips is difficult and also the desorption of furfural from these materials is not easy. Due to high reactivity of furfural the application of chemically active ion exchangers can lead to the formation of unwanted by-product.

The present invention relates to the process in which furfural is separated from its aqueous solutions using a bed of chemically inert polymer adsorbent. The polymer adsorbent is a porous copolymer of styrene and its derivatives with surface area higher than 30 m$^2$/g from which furfural is subsequently desorbed by an alcohol with 1-3 carbon atoms. In this process the polymer acts as a heterogenized extraction agent whose affinity toward furfural molecules is much higher than the affinity of water molecules.

Basic mechanism of furfural separation from water is its adsorption on the surface of polymer mass. Therefore, it is important to use a polymer adsorbent with well developed pore-wall area in dry state. There are known methods of preparation of such materials by synthesis of highly crosslinked copolymers of styrene and its derivatives in the presence of solvents. Standard method is the preparation of so called macroreticular resins by copolymerization of styrene with higher portion of divinylbenzene (more than 20%). Similar effect can be alternatively achieved by crosslinking of swollen styrene polymer by chloromethylation and subsequent Friedel-Crafts reaction, e.g. according to DDR Pat. No. DD 249,274. On adsorbents of this type, the furfural adsorption from aqueous solutions is very rapid. The effective dynamic capacity of the polymer adsorbent bed is practically equal to the equilibrium value resulting from the experiments at static conditions.

The bed of polymer adsorbent saturated by furfural is possible to regenerate by a solvent in which furfural is substantially better soluble than in water but which has small affinity toward the polymer, that is, a solvent in which the polymer does not swell. For this purpose alcohols with 1-3 carbon atoms are suitable. In the alcohol solution obtained during the regeneration, furfural was contained in concentration at least ten times higher than had been its concentration in original aqueous solution. The separation of furfural from alcoholic solution by adsorption separation is not complicated by the azeotrope formation and due to the low heat of vaporization of the alcohol, it is less energy-demanding than the distillation of aqueous solutions. The solvent used for the adsorbent regeneration can be recirculated.

In comparison with existing distillation processes, the adsorptive separation according to present invention is substantially more energy-efficient. This new process is also able to separate furfural from very diluted solutions containing less than 1% of furfural for which traditional methods using distillation or extraction are quite unsuitable.

EXAMPLE 1

Glass column 21×0.8 cm was packed with macroreticular styrene-divinylbenzene copolymer (divinylbenzene content 30%) having BET surface area of 130 m$^2$/g. The adsorbent had been wetted by methanol and then methanol was displaced by water. On this column, the stream of 1% furfural solution in water was introduced using flow rate of 0.8 cm$^3$/min. The samples collected in regular intervals at the column outlet were analyzed for their furfural content by liquid chromatography. After passing 40 cm of furfural solution through the column, the furfural concentration at the outlet was still lower than 0.005%. The column feed was then switched to methanol. All adsorbed furfural was eluted in 5 cm$^3$ of methanol with peak concentration 18%. After this regeneration it was possible to introduce the furfural solution again into the column. As the analysis of eluate has shown, the efficiency of the regenerated column was excellent.

EXAMPLE 2

From chloromethylated nonporous styrene-divinylbenzene copolymer (5% of divinylbenzene, 15% of chlorine), an adsorbent having the BET surface area 750 m$^2$/g was prepared by the method of crosslinking in swollen state described in DDR Pat. No. DD 249,274. In the test of its ability to adsorb furfural at the conditions described in Example 1, first traces of furfural in the eluate were observed after passing of 210 cm of 1% aqueous furfural solution through the column. During the regeneration furfural was desorbed from the column in 33 cm$^3$ of n-propanol.

We claim:

1. A method for the separation of furfural from a diluted aqueous solution comprising contacting a furfural containing aqueous solution with a polymer adsorbent which comprises porous crosslinked copolymers of styrene and derivatives thereof having an internal surface area greater than 30 m$^2$/g and desorbing furfural from the adsorbent by contacting said adsorbent with at least one alcohol containing from 1-3 carbon atoms.

* * * * *